US007613210B2

(12) United States Patent
Takehara

(10) Patent No.: US 7,613,210 B2
(45) Date of Patent: Nov. 3, 2009

(54) MEASURING TIME MANAGEMENT SYSTEM, DATA TRANSMITTER-RECEIVER AND MEASURING TIME MANAGEMENT METHOD

(75) Inventor: Katsumi Takehara, Tokyo (JP)

(73) Assignee: Tanita Corporation, Tokyo (JP)

( * ) Notice: Subject to any disclaimer, the term of this patent is extended or adjusted under 35 U.S.C. 154(b) by 438 days.

(21) Appl. No.: 11/727,405

(22) Filed: Mar. 26, 2007

(65) Prior Publication Data

US 2007/0286154 A1 Dec. 13, 2007

(30) Foreign Application Priority Data

Mar. 26, 2006 (JP) .............................. 2006-084341

(51) Int. Cl.
*H04L 12/26* (2006.01)
(52) U.S. Cl. ..................... 370/503; 370/350; 370/252; 370/328; 709/204; 709/224; 714/39; 714/47; 714/25; 707/10
(58) Field of Classification Search ................. 370/503, 370/350, 252, 328
See application file for complete search history.

(56) References Cited

U.S. PATENT DOCUMENTS

| 6,215,862 | B1 | 4/2001 | Lopes | |
|---|---|---|---|---|
| 6,659,861 | B1* | 12/2003 | Faris et al. ...................... | 463/1 |
| 7,063,665 | B2 | 6/2006 | Hasegawa et al. | |
| 2004/0003123 | A1 | 1/2004 | Kwon | |
| 2006/0233132 | A1* | 10/2006 | Lee ............................. | 370/328 |

FOREIGN PATENT DOCUMENTS

| JP | 2002-56099 | 2/2002 |
|---|---|---|
| JP | 2004-283570 | 10/2004 |
| JP | 2006-56998 | 3/2006 |

(Continued)

OTHER PUBLICATIONS

Copending U.S. Appl. No. 11/723,393, filed on Mar. 19, 2007, corresponds to JP 2006-75764.

(Continued)

*Primary Examiner*—Jude J Jean Gilles
(74) *Attorney, Agent, or Firm*—McDermott Will & Emery LLP

(57) ABSTRACT

A unified time can be simply set between data measuring instruments, and when the clock function of a specific data measuring instrument was damaged, the data measuring instrument can be immediately set to have the unified time, and when a certain data measuring instrument was managed with a plurality of PCs, it is not necessary to adjust the difference of time between the PCs, and in addition even when a data measuring instrument was used in the state with time zone difference, it is not necessary to adjust the difference of time due to the time zone difference. A PC 11 can obtain the time information of a provider side server 44 at the timing of transmitting measuring information to the provider side server 44 to synchronize therewith, and a relay key 12 can obtain the time information from the PC 11 to synchronize therewith. The relay key 12 records a time stamp on the measuring information transmitted from the data measuring instrument 14 or the like based on the above time information, and transmits to the PC 11 the measuring information on which the time stamp was recorded, and the PC 11 forwards the measuring information to the provider side server 44.

15 Claims, 9 Drawing Sheets

FOREIGN PATENT DOCUMENTS

| | | |
|---|---|---|
| JP | 2006-75764 | 3/2006 |
| WO | WO 01/88825 A2 | 11/2001 |
| WO | WO 02/00112 A2 | 1/2002 |
| WO | WO 2004/027676 A2 | 4/2004 |

OTHER PUBLICATIONS

Copending U.S. Appl. No. 11/713,105, filed on Mar. 2, 2007, corresponds to JP 2006-56998.

European Search Report, issued in Corresponding European Patent Application No. 07006088.4-1238, dated on Jun. 20, 2007.

* cited by examiner

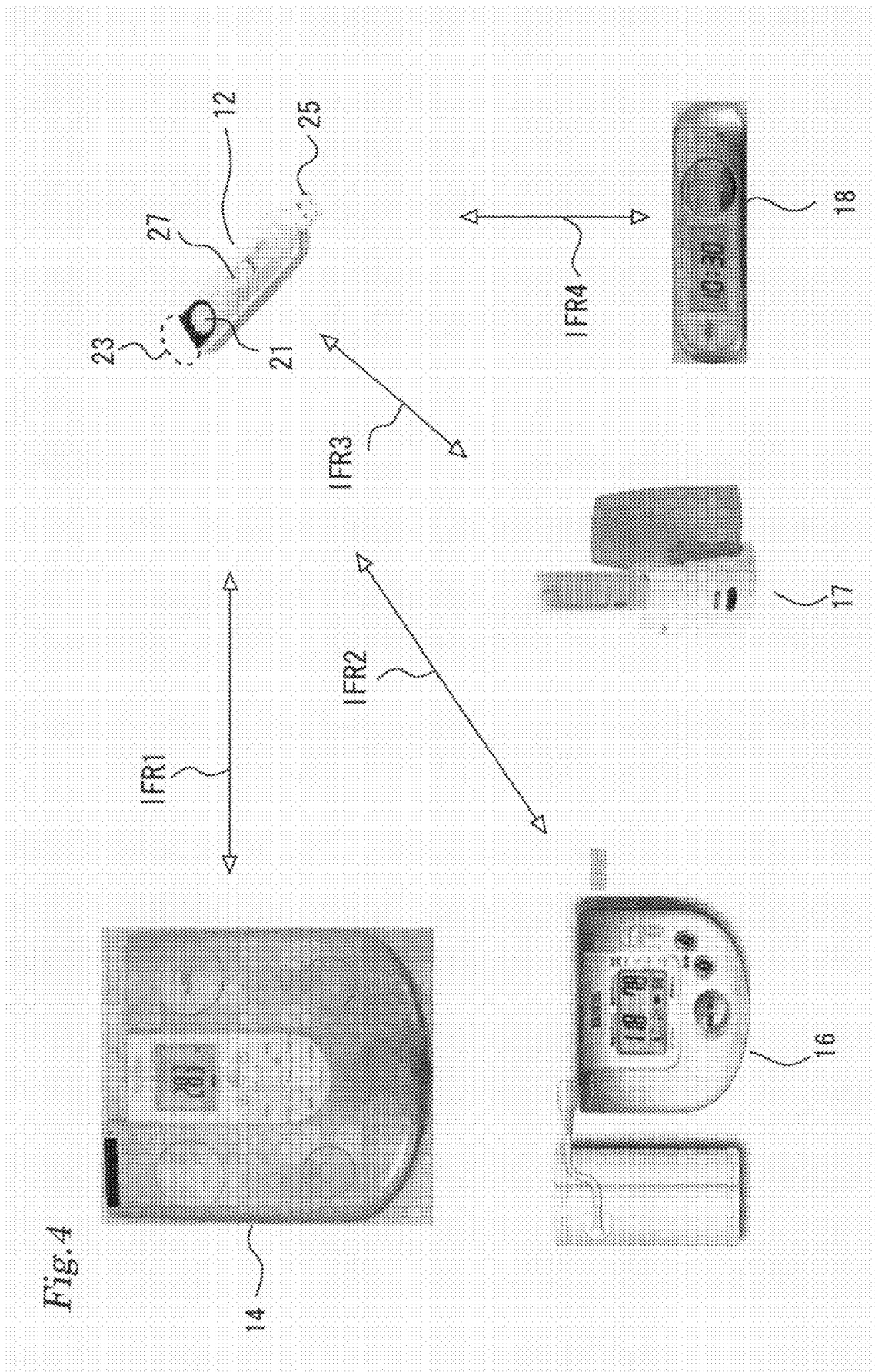

MEASURING TIME MANAGEMENT SYSTEM, DATA TRANSMITTER-RECEIVER AND MEASURING TIME MANAGEMENT METHOD

BACKGROUND OF THE INVENTION

1. Field of the Invention

The present invention relates to a measuring time management system including a server and an information terminal device connected to each other through a network, a data transmitter-receiver detachably connected with the information terminal device by a predetermined interface, and a data measuring instrument connected to the data transmitter-receiver by a predetermined wireless communication system.

2. Description of the Related Art

In recent years, there has been developed a system for performing health care by connecting a body composition monitor or the like to a personal computer (PC). In such a system, measurement time is managed by adding measured time (time) to measured data. In a conventional system, a clock function is provided for every data measuring instrument for the acquisition of measured time. For example, a clock function is prepared in an electronic sphygmomanometer to record a measured date and time (see "electronic sphygmomanometer", Jan. 30, 2003, <URL:http://www.citizen.co.jp/release/03/030130ud.htm>) or in a pedometer to record a measured date and time (see "pedometer" <URL: http://www.crecer.jp/seihin/HOSUU.htm>).

As mentioned above, in the conventional health care system, in order to obtain measured time used for the management of measurement time, the clock function is provided for every data measuring instrument. Accordingly, in order to set up the time unified between data measuring instruments, there has been a problem of requiring too much time. In particular, there has been a problem that when the clock function of a specific data measuring instrument was damaged, it requires too much time to set the unified time again, and thereby the data measuring instrument has not been able to be used for a long time. When a certain data measuring instrument was managed with a plurality of PCs, there has been a problem that it is necessary to adjust the difference of time between PCs. Furthermore, when a data measuring instrument was used in the state with time zone difference, there has been a problem that it is necessary to adjust the difference of time due to the time zone difference.

SUMMARY OF THE INVENTION

Thus, an object of the present invention made to solve the above problems is to provide a measuring time management system or the like in which unified time can be simply set between data measuring instruments, and when the clock function of a specific data measuring instrument was damaged, the data measuring instrument can be immediately set to have the unified time, and when a certain data measuring instrument was managed with a plurality of PCs, it is not necessary to adjust the difference of time between the PCs, and in addition even when a data measuring instrument was used in the state with time zone difference, it is not necessary to adjust the difference of time due to the time zone difference.

According to a first aspect of the present invention, there is provided a measuring time management system comprising: a server and an information terminal device connected to each other through a network, a data transmitter-receiver detachably connected with the information terminal device by a predetermined interface, and a data measuring instrument connected to the data transmitter-receiver by a predetermined wireless communication system, wherein the server includes time information transmitting means for transmitting the time information of the server side to the information terminal device, the information terminal device includes information terminal device side time information transmitting means for transmitting to the data transmitter-receiver the time information transmitted by the time information transmitting means, and measuring information forwarding means for forwarding to the server the measuring information transmitted from the data transmitter-receiver, the data transmitter-receiver includes data transmitter-receiver side synchronous means for synchronizing the time of the data transmitter-receiver with the time information transmitted by the information terminal device side time information transmitting means, information transmitting means for transmitting predetermined information to the data measuring instrument side, time stamp record means for recording a time stamp on the measuring information transmitted from the data measuring instrument based on the time information of the data transmitter-receiver side synchronized by the data transmitter-receiver side synchronous means, and time stamp recorded measuring information transmitting means for transmitting to the information terminal device the measuring information on which the time stamp was recorded by the time stamp record means.

According to a second aspect of the present invention, there is provided a data transmitter-receiver connected removably, by a predetermined interface, to an information terminal device connected to a server through a network, comprising: data transmitter-receiver side synchronous means for synchronizing the time of the data transmitter-receiver with the time information of the server side transmitted to the information terminal device, information transmitting means for transmitting to the data measuring instrument side the predetermined information containing the time information of the data transmitter-receiver side synchronized by the data transmitter-receiver side synchronous means, time stamp record means for recording a time stamp on the measuring information transmitted from the data measuring instrument based on the time information of the data transmitter-receiver side synchronized by the data transmitter-receiver side synchronous means, time stamp recorded measuring information transmitting means for transmitting to the information terminal device the measuring information on which the time stamp was recorded by the time stamp record means.

According to a third aspect of the present invention, there is provided a measuring time management method using a server and an information terminal device connected to each other through a network, a data transmitter-receiver detachably connected with the information terminal device by a predetermined interface, and a data measuring instrument connected to the data transmitter-receiver by a predetermined wireless communication system, wherein the server includes a time information transmitting step for transmitting the time information of the server side to the information terminal device, the information terminal device includes an information terminal device side time information transmitting step for transmitting to the data transmitter-receiver the time information transmitted at the time information transmitting step, and the data transmitter-receiver includes a data transmitter-receiver side synchronous step for synchronizing the time of the data transmitter-receiver with the time information transmitted at the information terminal device side time information transmitting step and an information transmitting step for transmitting predetermined information to the data measuring instrument side, the data measuring instrument includes a measuring information transmitting step for transmitting the measuring information to the data transmitter-receiver, the data transmitter-receiver includes a time stamp record step for recording a time stamp on the measuring information transmitted at the measuring information transmitting step based on the time information of the data transmitter-receiver side synchronized at the data transmitter-receiver side synchronous step and a time stamp recorded measuring information transmitting step for transmitting to the information terminal device the measuring information on which the time stamp was recorded at the time stamp record step, and the information terminal device includes a measuring information forwarding step for forwarding to the server the measuring information transmitted at the time stamp recorded measuring information transmitting step.

The above and other objects, effects, features and advantages of the present invention will become more apparent from the following description of the embodiments thereof taken in conjunction with the accompanying drawings.

BRIEF DESCRIPTION OF THE DRAWINGS

FIG. 4 shows the detailed configuration in the home system 10.

FIG. 5(A) is a flow chart illustrating the synchronous processing of the time when the relay key 12 is connected to the PC 11 for the first time in the state where there is no measured data of the data measuring instrument 14 or the like.

FIG. 8 is a flow chart illustrating the processing of the data measuring instrument of the type of urine glucose meter 17 or the like.

DETAILED DESCRIPTION OF THE PREFERRED EMBODIMENTS

Figure 1:
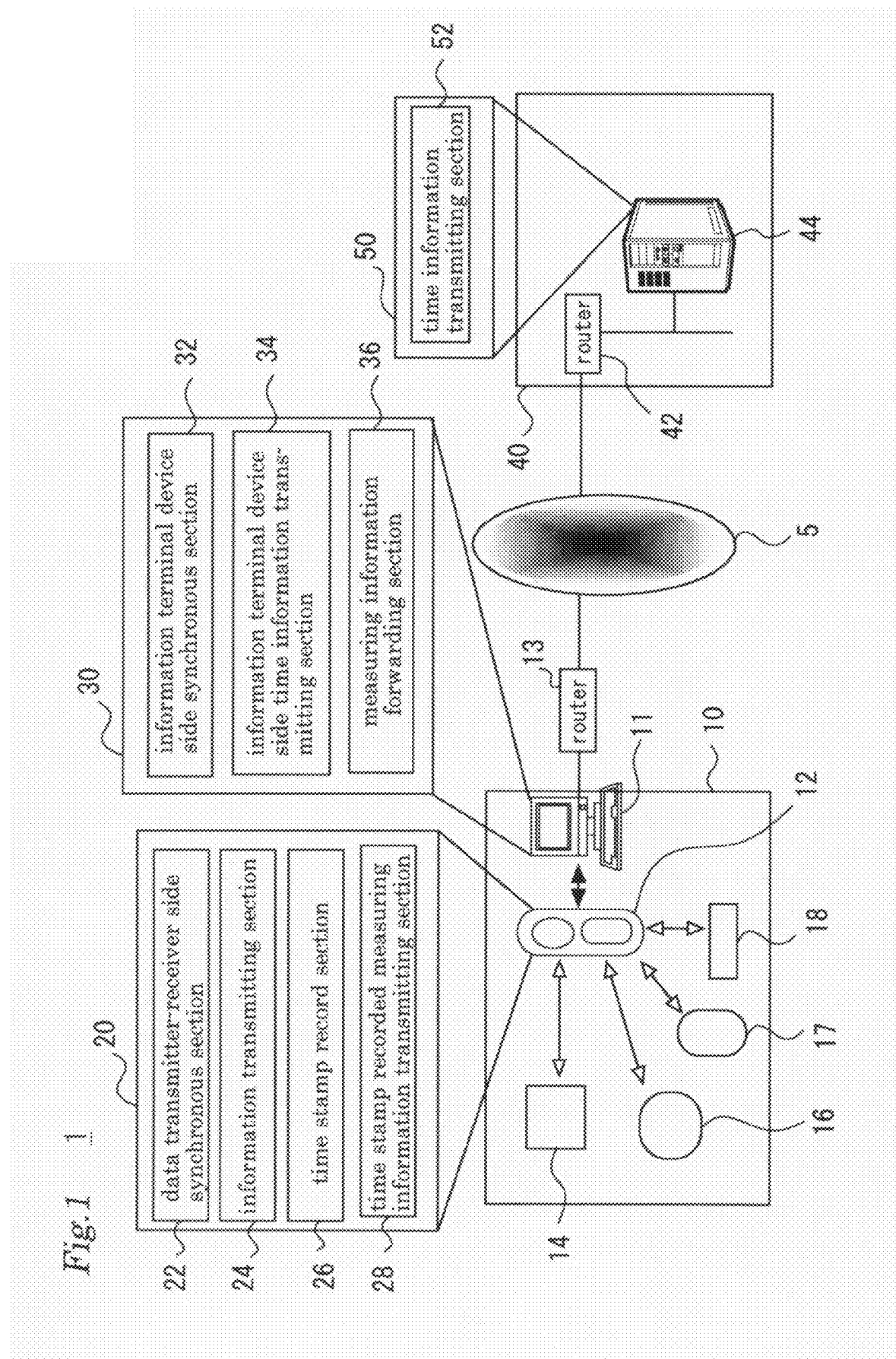
FIG. 1 shows a measuring time management system 1 in a first embodiment of the present invention.

Each embodiment will now be described in detail hereinafter with reference to the drawings. It is to be noted that the same or similar reference numerals are applied to the same or similar parts and elements throughout the drawings, and the description of the same or similar parts and elements will be omitted or simplified.

First Embodiment

FIG. 1 shows a measuring time management system 1 in a first embodiment of the present invention. In FIG. 1, a reference numeral 5 represents a network such as the Internet, a reference numeral 10 a home system of a person (a user, not shown) whose data for health care is measured, a reference numeral 11a. PC (an information terminal device) connected through the network 5 and a router 13, a reference numeral 40 a health care provider side system for managing the data for health care of the above user, a reference numeral 44 a server of the health care provider side system 40 connected through the network 5 and the router 42 (a server abbreviated as an "provider side server" hereinafter). As shown in FIG. 1, the PC 11 and the provider side server 44 are connected through the network 5.

In the home system 10 shown in FIG. 1, a reference numeral 12 is a relay key (data transmitter-receiver) detachably connected with the PC 11 with a predetermined interface, and reference numerals 14, 16, 17, and 18 are data measuring instruments (referred to as "data measuring instrument 14 or the like") connected to the relay key 12 by a predetermined wireless communication system (described later). As the predetermined interface, for example, a USB (Universal Serial Bus) can be used. Of course, an arbitrary interface can be used.

In FIG. 1, a reference numeral 50 is a functional block showing the function of the provider side server 44. As shown in FIG. 1, the provider side server 44 comprises a time information transmitting section (time information transmitting means) 52 which when the PC 11 detects the attaching of the relay key 12, after it receives the attaching information transmitted through the PC 11 and/or a request of the time information transmitted from the PC 11, it transmits the time information of the side of the provider side server 44 to the PC 11. Although absolute time may be used as the time, it is preferable to use relative time on the basis of predetermined time. For example, in the case of the date, when Jan. 1, 2000 is set to be 0 as the basis, Jan. 25, 2006 can be set to be 2,216. In the case of time, when 00:00:00 o'clock is set to be 0 as the basis, 11:43:15 o'clock can be set to be 42,195. In the case of a data measuring instrument that does not display the date and the time, the use of the relative time can make internal processing simpler.

Now, the function of the PC 11 will be described. In FIG. 1, a reference numeral 30 is a functional block showing the function of PC 11. As shown in FIG. 1, the PC 11 comprises a information terminal device side time information transmitting section (information terminal device side time information transmitting means) 34 for transmitting to the relay key 12 the time information transmitted from the time information transmitting section 52, and a measuring information forwarding section (measuring information forwarding means) 36 for forwarding to the provider side server 44 the measuring information transmitted from the relay key 12. The PC 11 may have the information terminal device side synchronous section (information terminal device side synchronous means) 32 for synchronizing the time of the PC 11 with the time information transmitted by the time information transmitting section 52. In this case, the information terminal device side time information transmitting section 34 can also transmit to the relay key 12 the time information of the PC 11 side synchronized by the information terminal device side synchronous section 32. Each of the above functions of the PC 11 and the provider side server 44 can be mainly realized with software.

In FIG. 1, a reference numeral 20 is a functional block showing the function of the relay key 12. As shown in FIG. 1, the relay key 12 has a clock function therein, keeps clocking even when being removed from the PC 11, and comprises a data transmitter-receiver side synchronous section (data transmitter-receiver side synchronous means) 22 for synchronizing the time of the relay key 12 with the time information transmitted by the information terminal device side time information transmitting section 34, an information transmitting section (information transmitting means) 24 for transmitting predetermined information to the data measuring instrument 14 or the like side, a time stamp record section (time stamp record means) 26 for recording a time stamp on the measuring information transmitted from the data measuring instrument 14 or the like based on the time information of the relay key 12 side synchronized by the data transmitter-receiver side synchronous section 22, a time stamp recorded measuring information transmitting section (time stamp recorded measuring information transmitting means) 28 for transmitting to the PC 11 the measuring information on which the time stamp was recorded by the time stamp record section 26. The predetermined information and predetermined measuring information, or the like, are stored in a memory (not shown) within the relay key, 12. The above functions can be realized by suitably combining hardware and software. As shown in FIG. 1, the data measuring instrument 14 or the like and the PC 11 are connected through the relay key 12, and after a time stamp is recorded by the time stamp record section 26 on the measured data measured in the data measuring instrument 14 or the like, it is forwarded to the PC 11 through the relay key 12. It is preferable to communicate between the data measuring instrument 14 or the like and the relay key 12 by a wireless communication system (predetermined wireless communication system) using infrared radiation, specified low power radio, or the like. The specified low power radio is radio without the need of license and short distance radio with the antenna power of 10 mW or less (radio equipment standard ARIBSTD-T67 for specified low power radio station telemeters, telecontrol, and data transmission). It is preferable to connect between the relay key 12 and the PC 11 with the interface of USB as mentioned above.

Figure 2:
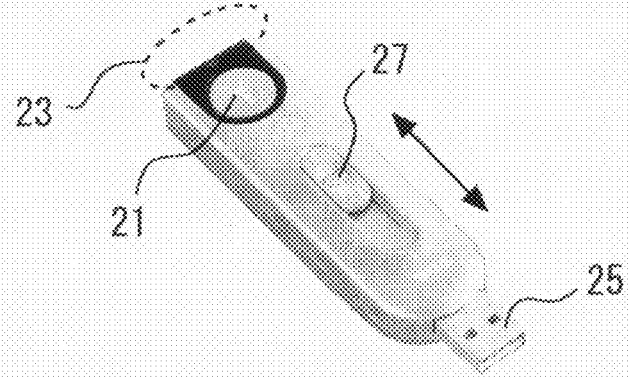
FIG. 2 shows the configuration of the relay key 12.

FIG. 2 shows the configuration of the relay key 12. In FIG. 2, the reference numeral 23 is an infrared transceiver (surrounded by a dotted line) used in order that the information transmitting section 24 transmits predetermined information to the data measuring instrument 14 or the like side. The predetermined information includes an activate instruction for activating the data measuring instrument 14 or the like, and personal setting information (user information), such as a measurement target person's height, age, or the like, requested by the data measuring instrument 14 or the like (for example, a body composition monitor). As described later, the predetermined information can also include the time information. The predetermined information is transmitted by pushing down a communication switch 21. When the above predetermined information is transmitted to the data measuring instrument 14 or the like, the data measuring instrument 14 or the like is automatically activated, based on the predetermined information, to measure the data such as body weight, and to transmit the measured data to the relay key 12 side. The measured data is received by the infrared transceiver 23. In FIG. 2, the reference numeral 25 is a USB terminal, in which by sliding a slide key 27 slide in the direction of an arrow shown in FIG. 2, the USB terminal 25 can be put out to the exterior of the relay key 12, or stored in the interior of the relay key 12. Since in an instrument using the conventional USB terminal, the USB terminal itself was always exposed to the instrument exterior, it was necessary to put a cap on it for the protection of the USB terminal. Although there has been a disadvantage that the cap is vulnerable to loss, according to the relay key 12 of the present invention, the cap can be eliminated by forming the slide key 27.

Figure 3:
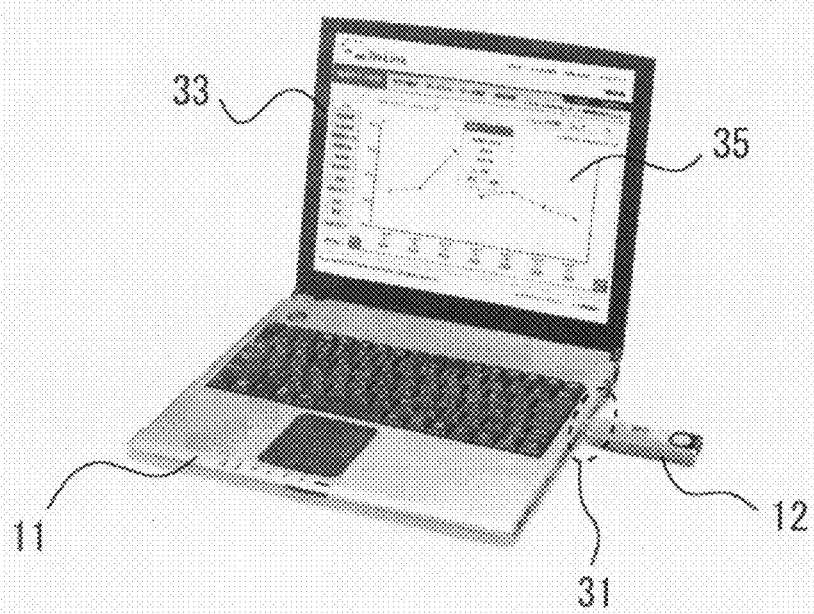
FIG. 3 shows the connection state between the relay key 12 and the PC 11.

FIG. 3 shows the connection state between the relay key 12 and the PC 11. As shown in FIG. 3, the USB terminal 25 of the relay key 12 can be connected to the USB port 31 of the PC 11 (not shown in FIG. 3, since it has connected). The provider side server 44 allows the measuring information stored in the database (not shown) to be read or browsed on the display 33 of the PC 11 in the various display formats 35 such as a graph and a table, as shown in FIG. 3.

FIG. 4 shows the detailed configuration in the home system 10. In FIG. 4, parts with the same reference numerals as those in FIGS. 1 and 2 represent the same elements, and the description thereof will be omitted. As shown in FIG. 4, the data measuring instruments 14, 16, 17 and 18 are a body composition monitor, a electronic sphygmomanometer, an urine glucose meter, and a pedometer, respectively. In FIG. 4, for the sake of convenience of drawing, although the relay key 12 is shown by the almost same size as other data measuring instrument 14 or the like, it actually has a compact size similar to a lighter (for example, 100 yen lighter in Japan). Preferably, the data measuring instrument 14 or the like is a measuring instrument for data related to a user's living body, and a thermometer other than above data measuring instruments 14 or the like can be included. Although four sets of data measuring instruments 14 or the like are shown in FIG. 4 for the convenience of drawing, the number is not necessarily limited to four sets and the data measuring instruments of the desired number can be provided. Communication system between the data measuring instruments 14, 16, 17, and 18 and the relay key 12 can be transceiver system by infrared INFR1, INFR2, INFR3, and INFR4, respectively. As a format of infrared transmission, the format of Association for Electric Home Appliances format or the like, or an original format or the like can be used. For example, by easy operation such as putting the pedometer 18 on the relay key 12, measured data can be automatically transmitted to the relay key 12.

The data measuring instrument 14 or the like includes one type of transmitting measured data (measuring information) to the relay key 12 side immediately after the measurement completion and another type of transmitting measuring information to the relay key 12 side after the lapse of the predetermined time after the measurement completion. As the former example, there are the body composition monitor 14, the electronic sphygmomanometer 16, or the like, all of which have the reception function of receiving the predetermined information transmitted from the information transmitting section 24. As the latter example, there are the urine glucose meter 17, the pedometer 18, or the like, and the urine glucose meter 17 has no reception function of receiving the predetermined information transmitted from the information transmitting section 24, while the pedometer 18 has the above reception function. This first embodiment will describe the data measuring instrument 14 or the like of the type of transmitting measuring information to the relay key 12 side immediately after the measurement completion, specifically the data measuring instrument 14 or the like of the type of body composition monitor 14, the electronic sphygmomanometer 16, or the like. The data measuring instrument 14 or the like in the first embodiment comprises a measuring information transmitting section (measuring information transmitting means, not shown) for transmitting to the relay key 12 the measuring information obtained by performing predetermined operation to measured data based on the predetermined information transmitted by the information transmitting section 24. A second embodiment will describe the data measuring instrument 14 or the like of the type of urine glucose meter 17 or the like. A third embodiment will describe the data measuring instrument 14 or the like of the type of pedometer 18 or the like.

Figure 5A:
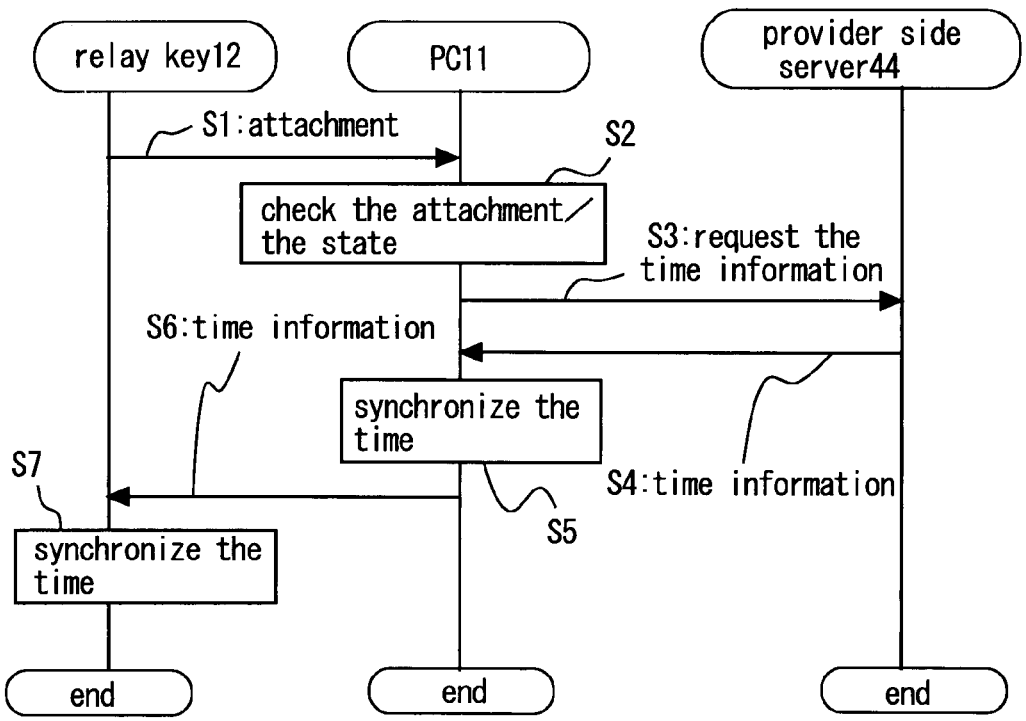

FIG. 5 is a flow chart illustrating a flow of the measuring time management method in the first embodiment of the present invention. FIG. 5 (A) shows synchronous processing of the time when the relay key 12 is connected to the PC 11 for the first time in the state where there is no measured data of the data measuring instrument 14 or the like. A left flow chart shows the flow of processing by the relay key 12 side, a central flow chart shows the flow of processing by the PC 11 side, a right flow chart shows the processing by the side of the provider side server 44, and lines connected between each flow chart show mutual communications. The detailed description in the processing blocks is omitted for the convenience of drawing. First, the relay key 12 is attached to the USB mount port of the PC 11 (Step S1). The PC 11 then checks the attachment of the relay key 12, and obtains the various state information of the relay key 12 (Step S2). This processing obtains the state of the relay key 12 at Step S30, as shown in the flow chart of FIG. 6. The state information representing the state includes, for example, battery state, the memory usage, or the like of the relay key 12. When it is determined that there is a problem in the state of the relay key 12 such as the low voltage level of the battery (Step S34), the error showing the problem is displayed on the display 33 of the PC 11 (Step S36), and the processing is terminated. When it is determined that there is no problem in particular (Step S34), the processing is terminated without doing anything. Subsequently, at Step S3 of FIG. 5(A), the PC 11 requests the time information from the provider side server 44 (Step S3). In response to this request, the provider side server 44 transmits to the PC 11 the time information from the time information transmitting section 52 (time information transmitting step, Step S4). The PC 11 synchronizes the time of the PC 11 with the received time information (Step S5). This time information includes a year, a month, a day, and a time. Furthermore, the PC 11 transmits to the relay key 12 the time information from the information terminal device side time information transmitting section 34 (information terminal device side time information transmitting step, Step S6). The relay key 12 synchronizes the time of the relay key 12 based-on this time information (the data transmitter-receiver side synchronous step, Step S7).

Figure 5B:
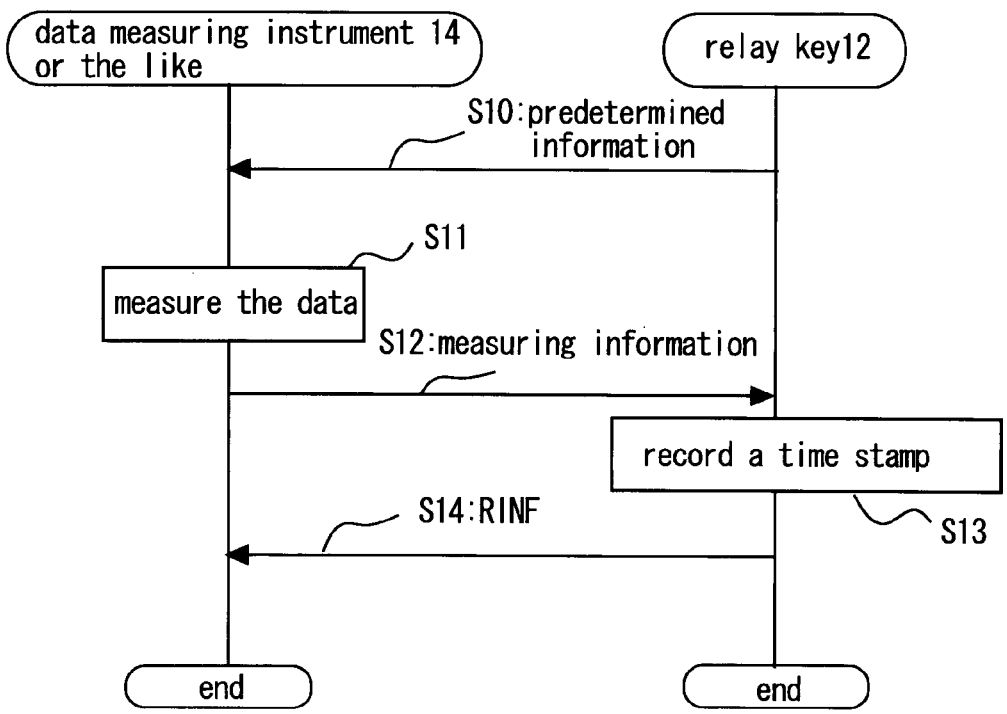
FIG. 5(B) is a flow chart illustrating the processing of the measured data between the relay key 12 and the body composition monitor 14 or the like when the relay key 12 is removed from the PC 11.
Figure 6:
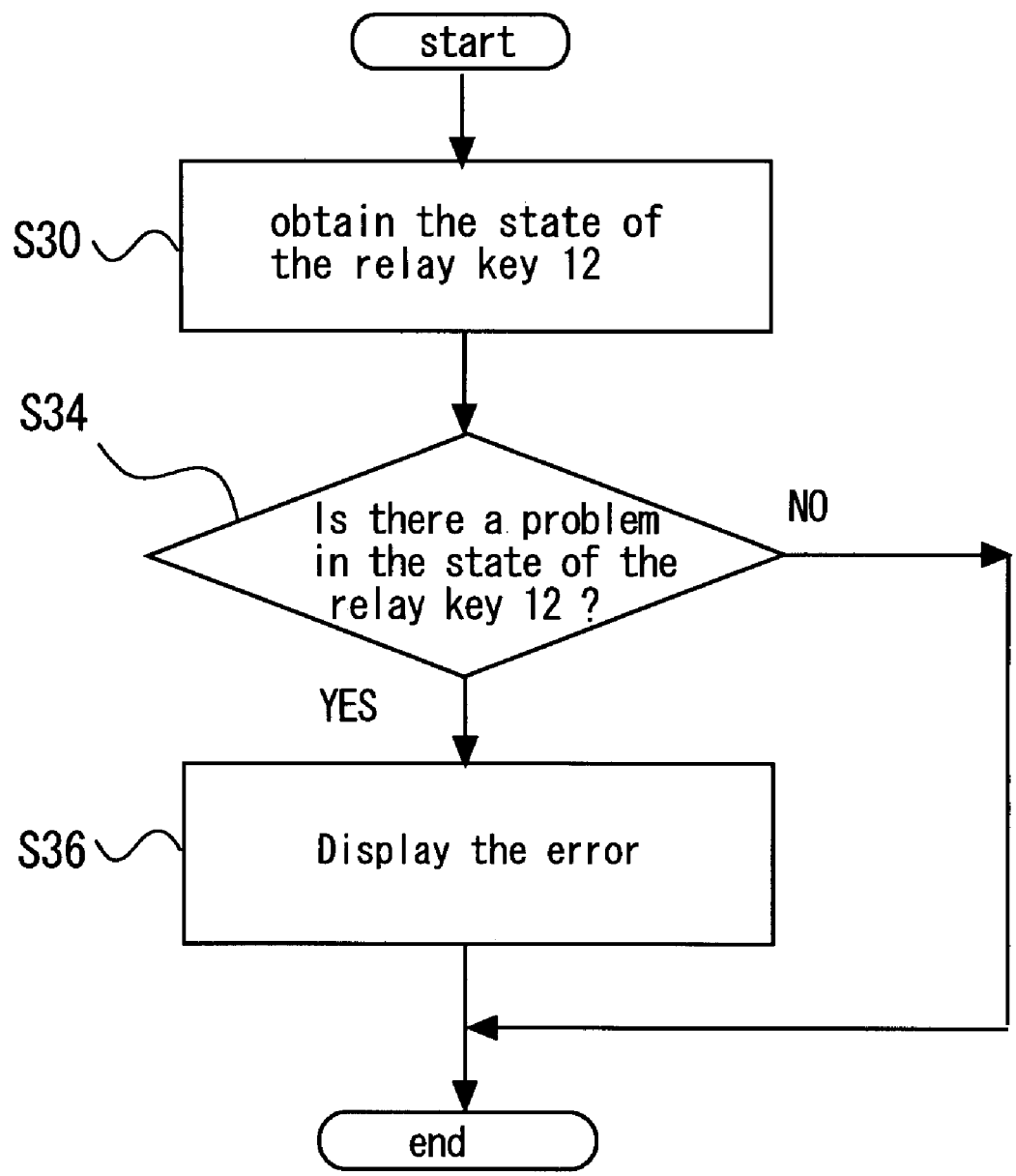
FIG. 6 is a flow chart illustrating the processing of step S30 and S32.

Next, the relay key 12 is removed from the PC 11, and the processing of the measured data between the relay key 12 and the body composition monitor 14 or the like that is a data measuring instrument will be described referring to FIG. 5(B). As shown in FIG. 5(B), first, a communication switch 21 of the relay key 12 is pushed down to transmit the predetermined information from the relay key 12 to the body composition monitor 14 or the like (information transmitting step, Step S10). This predetermined information is satisfied with only a user's body height, age, sex, or the like, and the time information of the relay key 12 side does not need to be included. Of course, the predetermined information including this time information may be transmitted, and the body composition monitor 14 may not use this time information, or may use it for the display section of the body composition monitor 14.

When this predetermined information is received by the body composition monitor 14 side or the like, a power source of the body composition monitor 14 side or the like which is always set as standby state will be started, and data measurement will be started (Step S11). Subsequently, when the data measurement is completed, the measured data is transmitted from the body composition monitor 14 side or the like to the relay key 12 (measuring information transmitting step, Step S12).

The relay key 12 records a time stamp on the measuring information transmitted at the measuring information transmitting step (Step S12) based on the time information inside the relay key 12, and stores it in the internal memory (time stamp record step, Step S13). When this storage is completed, the RINF signal of the reception check is transmitted from the relay key 12 to the body composition monitor 14 side or the like (Step S14), and the body composition monitor 14 side or the like will be again in the standby state for waiting the predetermined information from the relay key 12.

Next, in the case where the relay key 12 is attached to the PC 11, the processing of the measured data among the relay key 12, the PC 11, and the provider side server 44 will be described referring to FIG. 5(C). When the relay key 12 is attached to the PC 11, as described in the above FIG. 5(A) (Steps S1 through S7), the synchronous processing of the time of the relay key 12 and PC 11 will be made (Steps S15 through Step S21). When this synchronous processing is completed, the relay key 12 transmits to the PC 11 the measuring information on which the time stamp was recorded (time stamp recorded measuring information transmitting step, Step S22).

The PC 11 forwards the measuring information transmitted at the time stamp recorded measuring information transmitting step (Step S22) to the provider side server 44 (measuring information forwarding step, Step S23). In the provider side server 44, the forwarded measuring information is recorded therein and are concurrently performed various processing, and the result information is transmitted to the PC 11 (Step S24).

The PC 11 displays the transmitted result information on the display 33 in the various display formats (Step S25). Concurrently with this display, the PC 11 transmits to the relay key 12 an elimination signal for eliminating the measuring information transmitted at Step S22 (Step S26). The first processing is completed by the processing of FIG. 5(A) through FIG. 5(C), and from the next measurement, it is processed by the repeat of only the processing of FIG. 5(B) and FIG. 5(C).

Figure 5C:
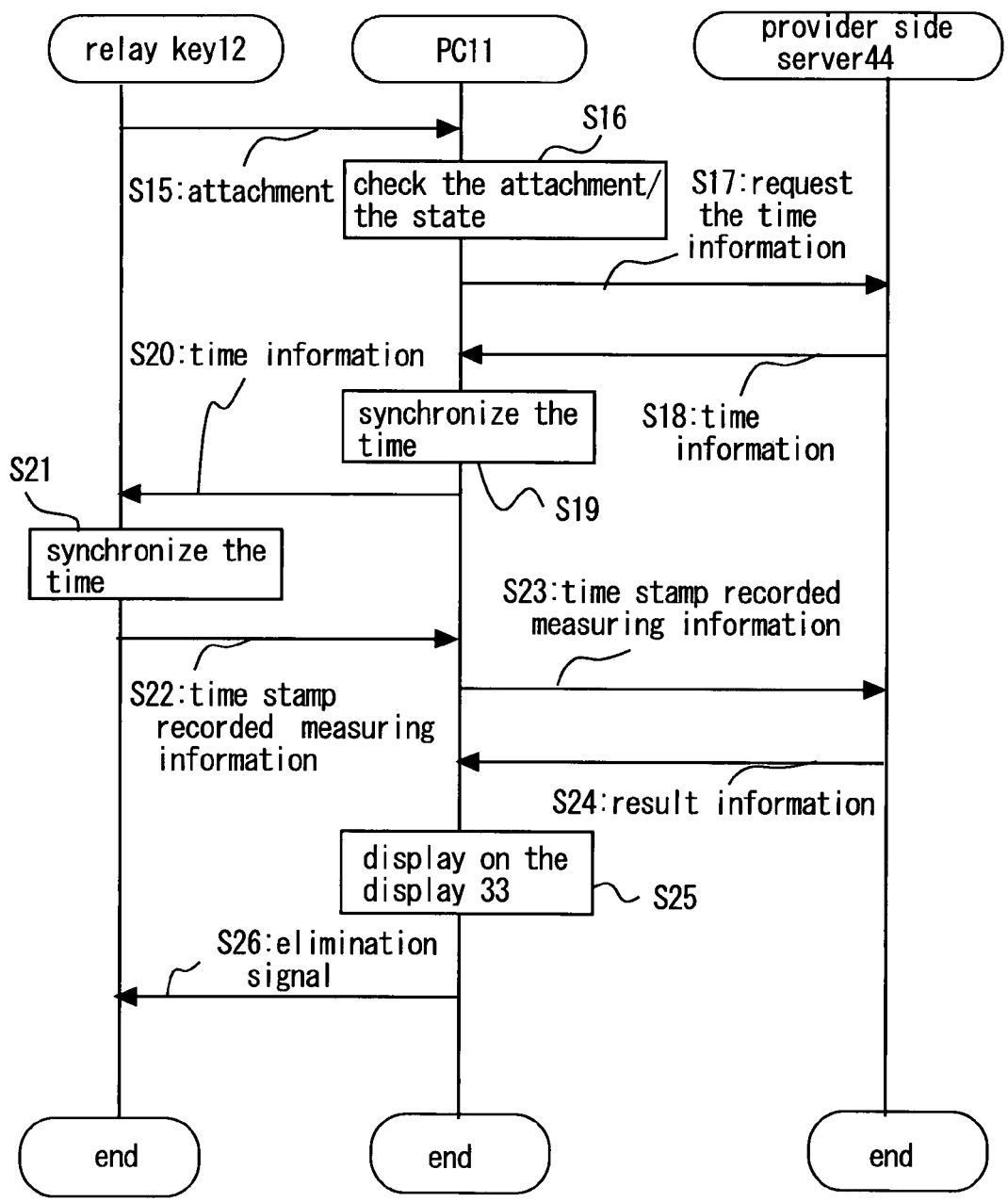
FIG. 5(C) is a flow chart illustrating the processing of the measured data among the relay key 12, the PC 11, and the provider side server 44 in the case where the relay key 12 is attached to the PC 11.
Figure 7A:
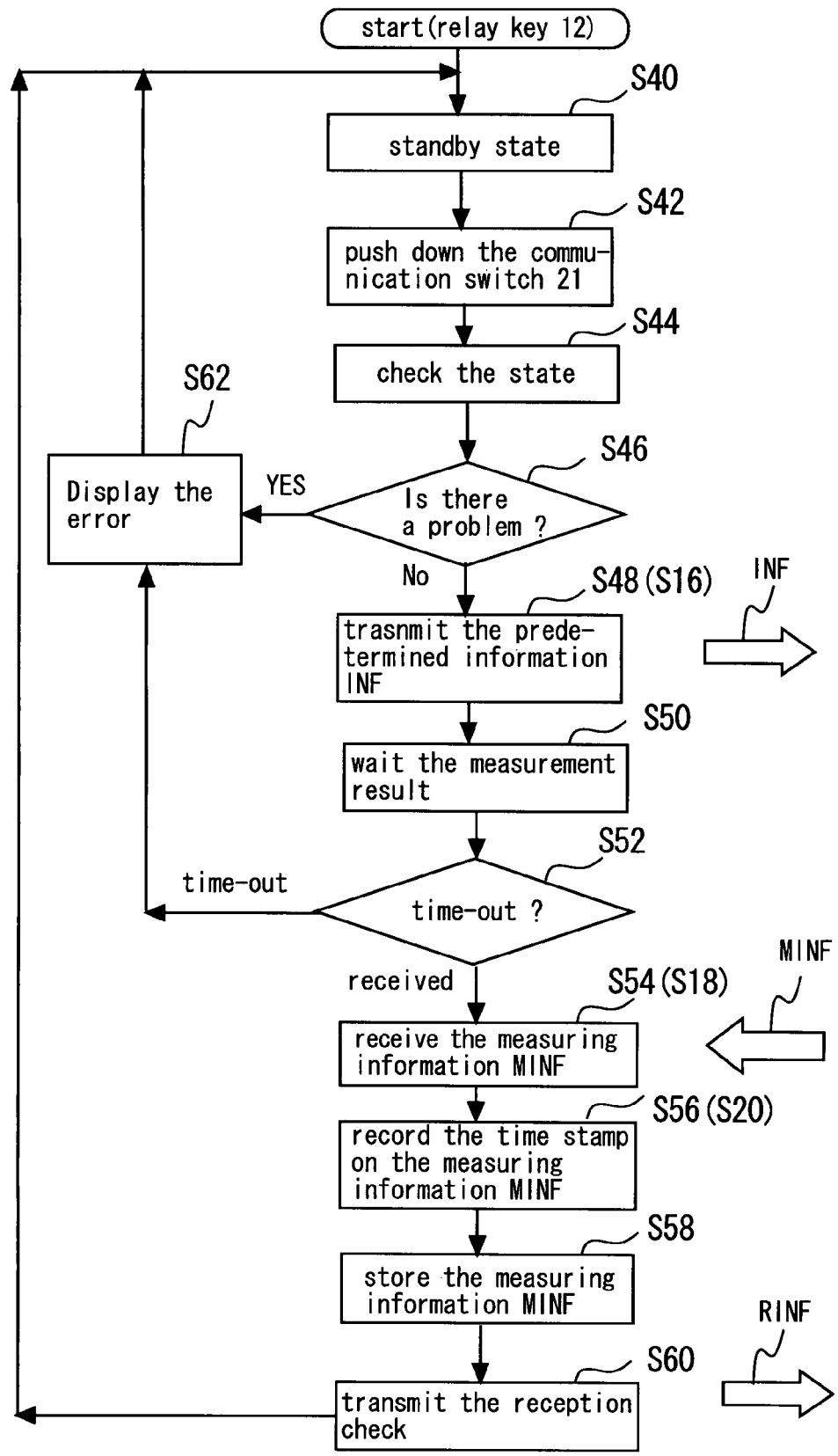
FIGS. 7(A) and 7(B) are flow charts illustrating the processing of the relay key 12 including other processing except for the processing related to the time information, the processing of the data measuring instrument of the type of body composition monitor 14 or the like, and communication between both.
Figure 7B:
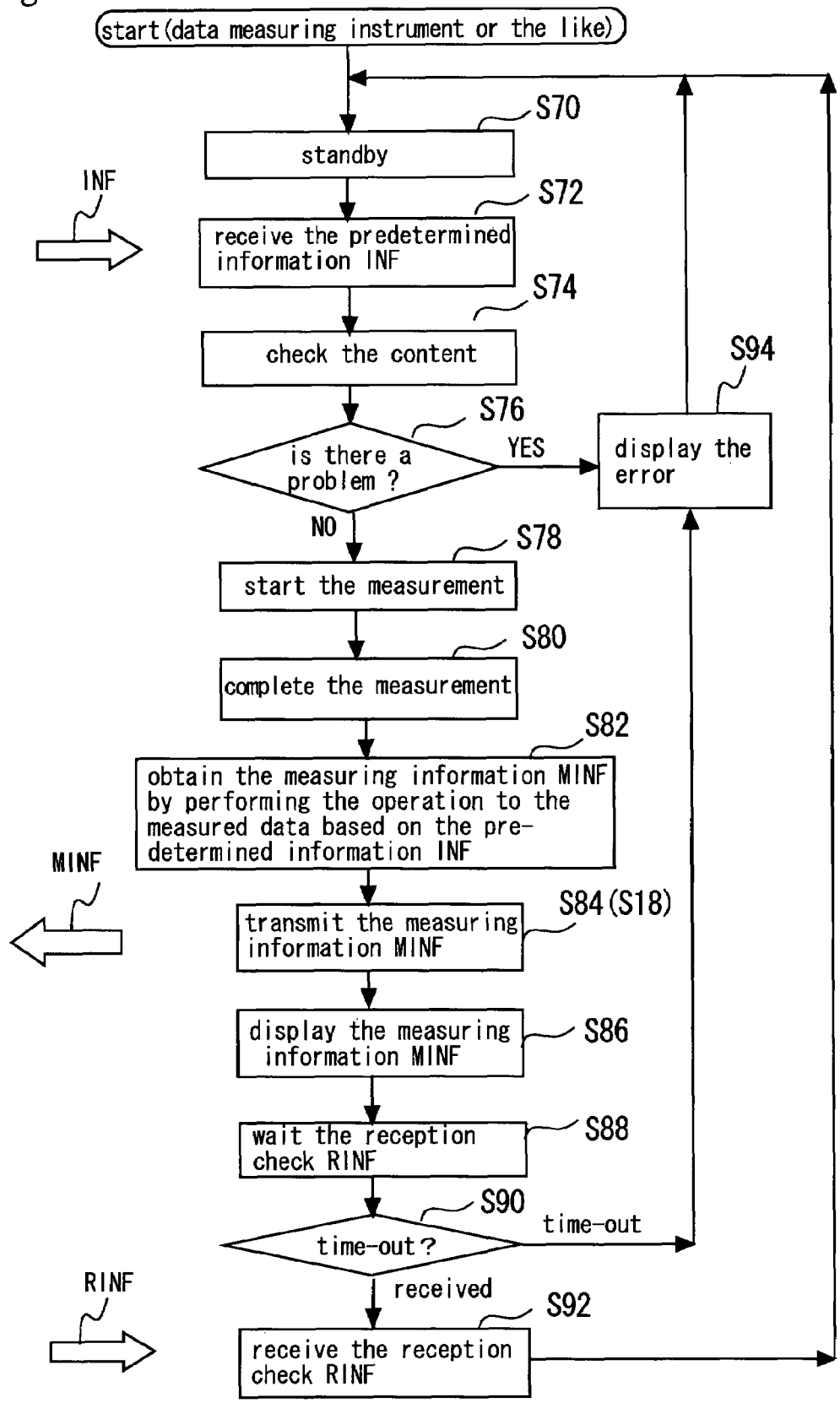

The flow chart shown in FIG. 5(A) through FIG. 5(C) shows the flow of processing related to the time information. FIGS. 7(A) and 7(B) are flow charts illustrating the processing of the relay key 12 including other processing except for the processing related to the time information, the processing of the data measuring instrument of the type of body composition monitor 14 or the like, and communication between both. FIG. 7(A) shows the processing of the relay key 12 side, FIG. 7(B) shows the processing of the data measuring instrument 14 side or the like, and the communications between both are shown by arrows. As shown in FIG. 7(A), after passing through the standby state (Step S40), the communication switch 21 is pushed down (Step S42) to check the state of the relay key 12 (Step S44). When it is determined that there is a problem in the state of the relay key 12 (Step S46), the error showing the problem is displayed on the display section (not shown) of the relay key 12 (Step S62), and the processing returns to the standby state (Step S40). The state of the relay key 12 includes the battery voltage, the amount of memory usage, or the like. As mentioned above, in the processing of Step S32 of the PC 11 side, the same processing is also performed in the state where the PC 11 and the relay key 12 are connected, but the relay key 12 side can also check independently the state in the state where the PC 11 and the relay key 12 are not connected. When it is not determined that there is a problem in particular in the state of the relay key 12 at Step S46, the predetermined information INF is transmitted (Step S48). Since the processing at Step S48 is the same as at Step S16 mentioned above, the processing is shown as S48 (S16) in the flow chart of FIG. 7A. Hereinafter, the similar notation will be used. Subsequently, the processing proceeds to the waiting state of the measurement result (Step S50), and when it is determined to be in the time-out (Step S52), the error showing the time-out is displayed (Step S62), and the processing returns to the standby state (Step S40). When the measuring information MINF is received before it is determined to be in the time-out (Step S52, S54 (S18)), the time stamp is recorded on the measuring information (Step S56 (S20)), and the measuring information on which the time stamp was recorded is stored (Step S58). Subsequently, the reception check RINF is then transmitted (Step S60), the processing returns to the standby state (Step S40), and the above processing is repeated. The predetermined information INF transmitted to the body composition monitor 14 or the like at Step S48 (S16) is satisfied with only the user information or the like, as mentioned above, but the unique ID of the relay key 12 can be also included. By including the unique ID in the measuring information MINF, when there are a plurality of relay keys 12 to the one data measuring instrument 14 or the like, the relay key 12 can check whether the measuring information MINF is transmitted thereto.

Next, the processing of the data measuring instrument 14 side or the like corresponding to the above processing of the relay key 12 side will be described. As shown in FIG. 7(B), after passing through the standby state (Step S70), when the predetermined information INF is received (Step S72), the contents of the predetermined information INF is checked (Step S74). When it is determined that there is a problem in the contents (Step S76), the error showing the problem is displayed on the display section (not shown) of the data measuring instrument 14 or the like (Step S94), and the processing returns to the standby state (Step S70). In the case that the data measuring instrument 14 or the like is the body composition monitor 14, as an example where a problem is included in the content, there is mentioned the case where the data of body height, sex, or the like is not contained in the content of the predetermined information INF. When it is determined that there is no problem in particular at Step S76, the measurement is started (Step S78) and the measured data is obtained. After the measurement completion (Step S80), based on the predetermined information INF, the measuring information MINF is obtained by performing the predetermined operation to the measured data (Step S82). The measuring information MINF is transmitted to the relay key 12 (Step S84 (S18)), and is displayed on the display section (not shown) (Step S86). The processing proceeds to the waiting state of the reception check RINF (Step S88), and when it is determined to be in the time-out (Step S90), the error showing the time-out is displayed (Step S94), and the processing returns to the standby state (Step S70). When the reception check RINF is received before it is determined to be in the time-out (Step S90, S92), the processing returns to the standby state (Step S70), and the above processing is repeated.

As mentioned above, according to the first embodiment of the present invention, the PC 11 can obtain the time information of the provider side server 44 at the timing of transmitting the measuring information to the provider side server 44, and it can synchronize with the time information. The relay key 12 can obtain the time information from the PC 11 to synchronize therewith. The relay key 12 records the time stamp on the measuring information transmitted from the data measuring instrument 14 or the like based on the time information synchronized as mentioned above, and transmits to the PC 11 the measuring information on which the time stamp was recorded. The PC 11 forwards the measuring information to the provider side server 44. As a result, since the time unified between data measuring instruments 14 or the like, i.e., the time information of the provider side server 44, can be simply set up, the time information with high accuracy can be always obtained. Even in the case where a certain data measuring instrument 14 or the like is managed with a plurality of PCs 11, since each PC 11 or the relay key 12 or the like is synchronized with the time information of the provider side server 44, it is not necessary to adjust the difference of time between the PCs 11. Furthermore, even in the case where the data measuring instrument 14 or the like is used in the state with the time zone difference, i.e., the data measuring instrument 14 or the like is used in a foreign country, since each PC 11 or the relay key 12 or the like is synchronized with the time information of the provider side server 44, the need for adjusting the difference of time due to the time zone difference can be eliminated.

Second Embodiment

Figure 8:
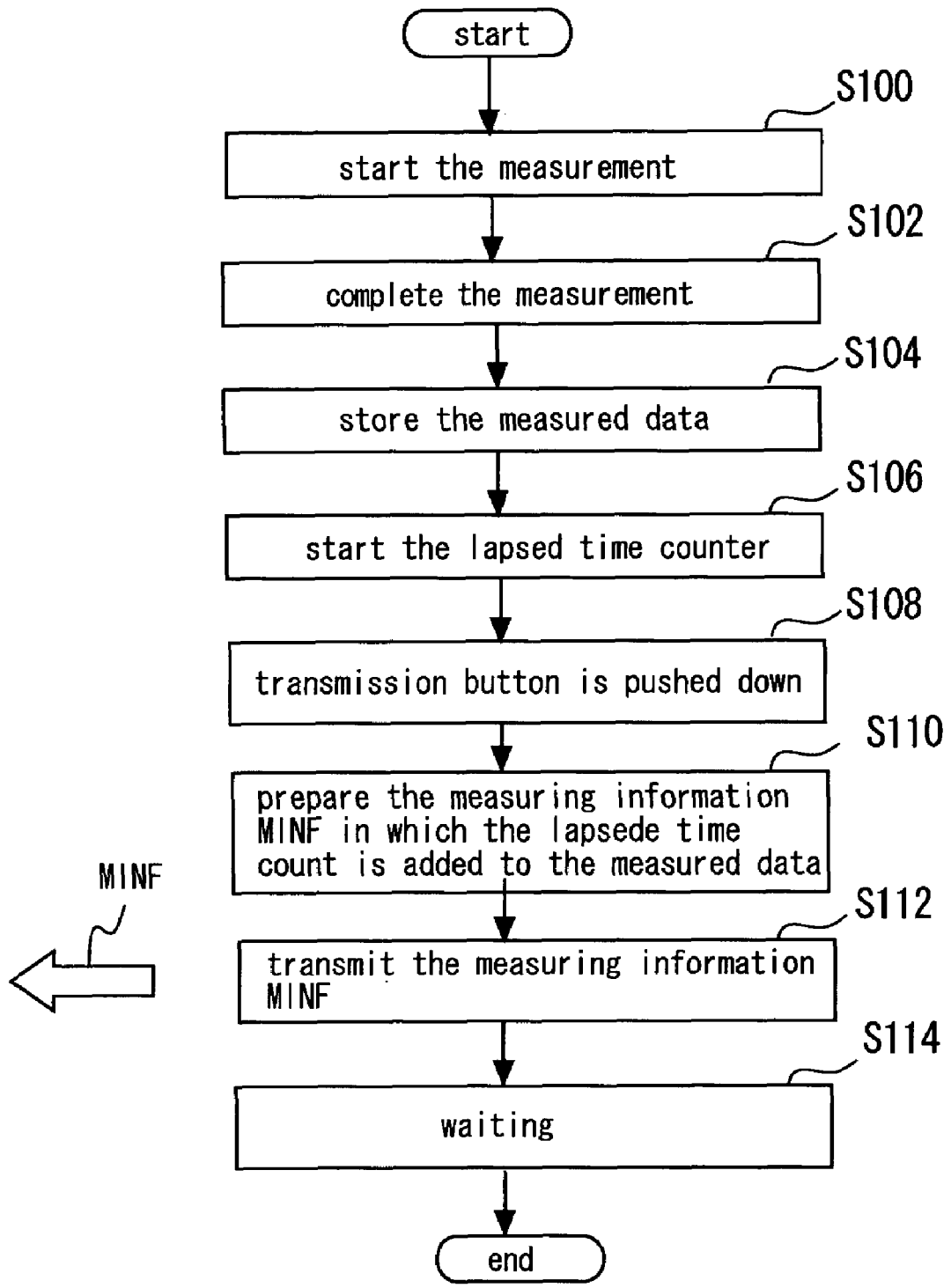

The second embodiment will describe the data measuring instrument of the type of urine glucose meter 17 or the like in which after the lapse of predetermined time after the measurement completion, the measuring information is transmitted to the relay key 12. FIG. 8 is a flow chart illustrating the processing of the data measuring instrument of the type of urine glucose meter 17 or the like. Since the processing of the corresponding relay key 12 side is the same as that of the flow chart shown in FIG. 7(A), the description will be omitted. As shown in FIG. 8, the measurement is started (Step S100) and the measured data is obtained. After the measurement completion (Step S102), the measured data is stored in the memory (not shown) of the data measuring instrument 14 or the like (Step S104). The count of lapsed time is then started at the lapsed time counter inside the urine glucose meter 17 or the like (Step S106). When the transmission button (not shown) of the data measuring instrument 17 or the like is pushed down (Step S108), the count of the lapsed time counter will be stopped at this timing. Subsequently, there is prepared the measuring information MINF in which the lapsed time from the measurement completion to the transmission of the measuring information (lapsed time information) counted with the lapsed time counter is added to the measured data (Step S110). After the measuring information MINF is transmitted (Step S112), the processing proceeds to the waiting state (Step S114).

Although the relay key 12 transmits the predetermined information INF as shown in FIG. 7(A) (Step S48 (S16)), since the data measuring instrument of the type of urine glucose meter 17 or the like does not have the reception function as mentioned above, the predetermined information INF is not received. Furthermore, although the relay key 12 transmits the reception check RINF as shown in FIG. 7(A) (Step S60), since the data measuring instrument of the type of urine glucose meter 17 or the like does not have the reception function as mentioned above, this reception check RINF is not also received.

After a time stamp is recorded by the relay key 12 on the measuring information MINF to which the lapsed time was added (Step S56 (S20)), the measuring information MINF is transmitted to the provider side server 44 through the PC 11 (Step S22, S24). Since the lapsed time (T) is time (T=S−E) which is given by subtracting the measurement completion time (time (E) at Step S102) from the time (S) when the measuring information was transmitted, i.e., the time when the time stamp was recorded, the measurement completion time can be obtained by the inverse operation of subtracting the lapsed time (T) from the time (S) shown with the time stamp (S−T=S−(S−E)=E). The PC 11 can comprise such the inverse operation as calculation means (calculation step in the measuring time management method) for calculating the measurement completion time based on the time stamp recorded on the measuring information transmitted by the time stamp recorded measuring information transmitting section 28, and the lapsed time contained in the measuring information. Alternatively, the provider side server 44 can also comprise such the inverse operation as calculation means (calculation step) for calculating the measurement completion time based on the time stamp recorded on the measuring information forwarded by the measuring information forwarding section 36, and the lapsed time contained in the measuring information.

As mentioned above, according to the second embodiment of the present invention, the measuring time management system or the like of the present invention can be also applied to the data measuring instrument of the type of urine glucose meter 17 or the like in which after the lapse of the predetermined time after the measurement completion, the measuring information is transmitted to the relay key 12. In the data measuring instrument of the type of urine glucose meter 17 or the like, after the measurement completion, the count of the lapsed time counter is started and the count of the lapsed time counter will be stopped at the timing at which the transmission button was pushed down. The measuring information MINF, in which the lapsed time from the measurement completion to the transmission of the measuring information counted with the lapsed time counter is added to the measured data, is prepared and transmitted. The measurement completion time can be obtained by the inverse operation of subtracting the lapsed time (T) from the time (S) shown with the time stamp. The PC 11 can comprise such the inverse operation as the calculation means for calculating the measurement completion time based on the time stamp recorded on the measuring information transmitted by the time stamp recorded measuring information transmitting section 28, and the lapsed time contained in the measuring information. Alternatively, the provider side server 44 can comprise such the inverse operation as the calculation means for calculating the measurement completion time based on the time stamp recorded on the measuring information forwarded by the measuring information forwarding section 36, and the lapsed time contained in the measuring information. Since the time of the PC 11 synchronizes with the time information of the provider side server 44, the time stamp with high accuracy can be always recorded on the measuring information.

Third Embodiment

The third embodiment will describe the data measuring instrument of the type of pedometer 18 or the like in which, in a manner similar to the urine glucose meter 17 or the like of the second embodiment, after the lapse of predetermined time after the measurement completion, the measuring information is transmitted to the relay key 12 side, and which has the reception function of receiving the predetermined information transmitted from the information transmitting section 24. The processing of the relay key 12 side is the same except for the difference in a part of processing of Step S48 (S16) in the flow chart shown in FIG. 7(A). The predetermined information INF transmitted at Step S48 (S16) includes the time information of the relay key 12 side synchronized by the data transmitter-receiver side synchronous section 22. Since other processing is the same, the description will be omitted.

In the processing of the pedometer 18 side, some processing is partially added to the processing of Step S74 in the flow chart of FIG. 7(B), and the processing of Step S82 is replaced with the processing from Step S104 through Step S110 of the flow chart of FIG. 8. For this reason, the parts of an addition and replacement will be described and the description about the same processing will be omitted. At Step S74 shown in FIG. 7(B), in addition to the check of the contents of predetermined information INF, the processing in which the data measuring instrument 18 or the like synchronizes the time of the data measuring instrument 18 with the time information contained in the predetermined information INF (data measuring instrument side synchronous step) is included. The data measuring instrument side synchronous step is performed by the data measuring instrument side synchronous section (data measuring instrument side synchronous means, not shown) that the data measuring instrument 18 or the like has. After the measurement completion (Step S80), instead of the processing of Step S82, the processing from Step S104 to Step S110 in the flow chart of FIG. 8 is performed. In other words, the measured data is stored in the memory of the pedometer 18 side (not shown) (Step S104). The count of the lapsed time counter is then started (step S106). When the transmission button (not shown) of the pedometer 18 is pushed down (Step S108), the count of the lapsed time counter will be stopped at this timing. Subsequently, the measuring information MINF, in which the lapsed time from the measurement completion to the transmission of the measuring information counted with the lapsed time counter is added to the measured data, is prepared (Step S110). Hereinafter, the processing from Step S84 (S18) (the transmission of the measuring information MINF) in the flow chart shown in FIG. 7(B) is performed. Since the pedometer 18 has the reception function, a confirmation processing (Steps S88 through S92) of the reception check RINF is similarly performed.

As mentioned above, according to the third embodiment of the present invention, the measuring time management system or the like of the present invention can be applied to the data measuring instrument of the type of pedometer 18 or the like in which, in a manner similar to the urine glucose meter 17 or the like of the second embodiment, after the lapse of the predetermined time after the measurement completion, the measuring information is transmitted to the relay key 12 side, and which has the reception function of receiving the predetermined information transmitted from the information transmitting section 24. The data measuring instrument of the type of pedometer 18 or the like comprises the data measuring instrument side synchronous section for synchronizing with the time information transmitted from the relay key 12. For this reason, even when the clock function of the data measuring instrument of the type of pedometer 18 or the like was damaged, by synchronizing with the time information transmitted from the relay key 12, the data measuring instrument of the type of pedometer 18 or the like can be simply set to have the unified time with high accuracy. It should be noted that although, in the embodiments of the present invention, the time of the PC 11 is synchronized with the time of the server 44, in the case where it is not preferable to change the time of the PC 11 without seeking permission from the user, the PC 11 does not synchronize the time information, when the relay key 12 is put in the PC 11, the PC 11 accesses to the server 44 to obtain the time information and the PC 11 only forwards the time information from the server 44 to the relay key 12, and only the relay key 12 may synchronize with the time information.

INDUSTRIAL APPLICABILITY

As an example of practical use of the present invention, there can be mentioned the health care system for a person, such as a company employee, who does not make an allowance for time to input measured data into a PC for himself because of being busy, or a person, such as an elderly person living alone, who is unfamiliar with and faces difficulty in the operation of a PC or the like.

According to the measuring time management system or the like of the present invention, a PC can obtain the time information of a provider side server at the timing of transmitting measuring information to the provider side server, and it can synchronize with the time information. A relay key can obtain the time information from the PC to synchronize therewith. The relay key records a time stamp on the measuring information transmitted from the data measuring instrument based on the time information synchronized as mentioned above, and transmits to the PC the measuring information on which the time stamp was recorded. The PC forwards the measuring information to the provider side server. As a result, since the time unified between data measuring instruments, i.e., the time information of the provider side server, can be simply set up, the time information with high accuracy can be always obtained. Even in the case where a certain data measuring instrument is managed with a plurality of PCs, since each PC or the relay key is synchronized with the time information of the provider side server, it is not necessary to adjust the difference of time between the PCs. Furthermore, even in the case where the data measuring instrument is used in the state with the time zone difference, i.e., it is used in a foreign country, since the PC or the relay key is synchronized with the time information of the provider side server, there is an effect that the need for adjusting the difference of time due to the time zone difference can be eliminated.

In the measuring time management system, the data measuring instrument may include measuring information transmitting means for transmitting to the data transmitter-receiver the measuring information obtained by performing predetermined operation to measured data based on the predetermined information transmitted by the information transmitting means.

In the measuring time management system, when the data measuring instrument transmits the measuring information after the lapse of the predetermined time after measurement completion, the measuring information transmitted from the data measuring instrument to the data transmitter-receiver may contain lapsed time information showing the lapsed time from the measurement completion to the transmission of the measuring information, the information terminal device may include a calculation means for calculating measurement completion time based on the time stamp recorded on the measuring information transmitted by the time stamp recorded measuring information transmitting means, and the lapsed time information contained in the measuring information, or the server may include the calculation means for calculating the measurement completion time based on the time stamp recorded on the measuring information forwarded by the measuring information forwarding means, and the lapsed time information contained in the measuring information.

In the measuring time management system, the predetermined information transmitted by the information transmitting means may include the time information of the data transmitter-receiver side synchronized by the data transmitter-receiver side synchronous means, when the data measuring instrument performs the synchronization with the time information, the data measuring instrument may further include data measuring instrument side synchronous means for synchronizing the time of the data measuring instrument with the time information.

In the measuring time management system, the time information may be relative time on the basis of the predetermined time.

In the data transmitter-receiver, the measuring information transmitted from the data measuring instrument in the time stamp record means may be obtained by performing predetermined operation to measured data with the data measuring instrument based on the predetermined information transmitted by the information transmitting means.

In the data transmitter-receiver, when the data measuring instrument transmits the measuring information after the lapse of predetermined time after measurement completion, the measuring information transmitted from the data measuring instrument to the data transmitter-receiver may contain lapsed time information showing the lapsed time from the measurement completion to the transmission of the measuring information, measurement completion time may be calculated by the information terminal device based on the time stamp recorded on the measuring information transmitted by the time stamp recorded measuring information transmitting means, and the lapsed time information contained in the measuring information, or the measurement completion time may be calculated by the server based on the time stamp recorded on the measuring information transmitted from the information terminal device, and the lapsed time information contained in the measuring information.

In the data transmitter-receiver, the predetermined information transmitted by the information transmitting means may include the time information of the data transmitter-receiver side synchronized by the data transmitter-receiver side synchronous means, when the data measuring instrument performs the synchronization with the time information, the time of the data measuring instrument is synchronized with the time information by the data measuring instrument.

In the data transmitter-receiver, the time information may be relative time on the basis of the predetermined time.

In the measuring time management method, the measuring information transmitting step may transmit to the data transmitter-receiver the measuring information performed predetermined operation to measured data based on the predetermined information transmitted at the information transmitting step.

In the measuring time management method, when the data measuring instrument transmits the measuring information after the lapse of predetermined time after measurement completion, the measuring information transmitted at the measuring information transmitting step may contain lapsed time information showing lapsed time from the measurement completion to the transmission of the measuring information, the information terminal device may include a calculation step for calculating measurement completion time based on the time stamp recorded on the measuring information transmitted at the time stamp recorded measuring information transmitting step, and the lapsed time information contained in the measuring information, or the server may include the calculation step for calculating the measurement completion time based on the time stamp recorded on the measuring information forwarded at the measuring information forwarding step, and the lapsed time information contained in the measuring information.

In the measuring time management method, the predetermined information transmitted at the information transmitting step may include the time information of the data transmitter-receiver side synchronized at the data transmitter-receiver side synchronous step, and when the data measuring instrument performs the synchronization with the time information, the data measuring instrument may further include a data measuring instrument side synchronous step for synchronizing the time of the data measuring instrument with the time information prior to the measuring information transmitting step.

In the measuring time management method, the time information may be relative time on the basis of the predetermined time.

The present invention has been described in detail with respect to various embodiments, and it will now be apparent from the foregoing to those skilled in the art that changes and modifications may be made without departing from the invention in its broader aspects, and it is the invention, therefore, in the appended claims to cover all such changes and modifications as fall within the true spirit of the invention.

The entire disclosure of Japanese Patent Application No. 2006-084341 filed on Mar. 26, 2006 including specification, claims, drawings and summary are incorporated herein by reference in its entirety.

What is claimed is:

1. A measuring time management system comprising: a server and an information terminal device connected to each other through a network, a data transmitter-receiver detachably connected with the information terminal device by a predetermined interface, and a data measuring instrument connected to the data transmitter-receiver by a predetermined wireless communication system, wherein
said server includes
time information transmitting means for transmitting the time information of the server side to said information terminal device,
said information terminal device includes
information terminal device side time information transmitting means for transmitting to said data transmitter-receiver the time information transmitted by said time information transmitting means, and
measuring information forwarding means for forwarding to said server the measuring information transmitted from said data transmitter-receiver,
said data transmitter-receiver includes
data transmitter-receiver side synchronous means for synchronizing the time of the data transmitter-receiver with the time information transmitted by said information terminal device side time information transmitting means,
information transmitting means for transmitting predetermined information to said data measuring instrument side,
time stamp record means for recording a time stamp on the measuring information transmitted from said data measuring instrument based on the time information of the data transmitter-receiver side synchronized by said data transmitter-receiver side synchronous means, and
time stamp recorded measuring information transmitting means for transmitting to said information terminal device the measuring information on which the time stamp was recorded by said time stamp record means.

2. The measuring time management system according to claim 1, wherein said data measuring instrument includes measuring information transmitting means for transmitting to said data transmitter-receiver the measuring information obtained by performing predetermined operation to measured data based on the predetermined information transmitted by said information transmitting means.

3. The measuring time management system according to claim 1, wherein when said data measuring instrument transmits the measuring information after the lapse of the predetermined time after measurement completion, the measuring information transmitted from said data measuring instrument to said data transmitter-receiver contains lapsed time information showing the lapsed time from the measurement completion to the transmission of the measuring information,
said information terminal device includes a calculation means for calculating measurement completion time based on the time stamp recorded on the measuring information transmitted by said time stamp recorded measuring information transmitting means, and the lapsed time information contained in the measuring information, or
said server includes the calculation means for calculating the measurement completion time based on the time stamp recorded on the measuring information forwarded by said measuring information forwarding means, and the lapsed time information contained in the measuring information.

4. The measuring time management system according to claim 3, wherein the predetermined information transmitted by said information transmitting means includes the time information of said data transmitter-receiver side synchronized by said data transmitter-receiver side synchronous means, when said data measuring instrument performs the synchronization with the time information, said data measuring instrument further includes data measuring instrument side synchronous means for synchronizing the time of said data measuring instrument with the time information.

5. The measuring time management system according to claim 1, the time information is relative time on the basis of the predetermined time.

6. A data transmitter-receiver connected removably, by a predetermined interface, to an information terminal device connected to a server through a network, comprising:
data transmitter-receiver side synchronous means for synchronizing the time of the data transmitter-receiver with the time information of the server side transmitted to the information terminal device,
information transmitting means for transmitting to the data measuring instrument side the predetermined information containing the time information of the data transmitter-receiver side synchronized by said data transmitter-receiver side synchronous means,
time stamp record means for recording a time stamp on the measuring information transmitted from the data measuring instrument based on the time information of the data transmitter-receiver side synchronized by said data transmitter-receiver side synchronous means,
time stamp recorded measuring information transmitting means for transmitting to the information terminal device the measuring information on which the time stamp was recorded by said time stamp record means.

7. The data transmitter-receiver according to claim 6, wherein the measuring information transmitted from the data measuring instrument in said time stamp record means is obtained by performing predetermined operation to measured data with the data measuring instrument based on the predetermined information transmitted by said information transmitting means.

8. The data transmitter-receiver according to claim 6, wherein when the data measuring instrument transmits the measuring information after the lapse of predetermined time after measurement completion, the measuring information transmitted from the data measuring instrument to the data transmitter-receiver contains lapsed time information showing the lapsed time from the measurement completion to the transmission of the measuring information, measurement completion time is calculated by the information terminal device based on the time stamp recorded on the measuring information transmitted by said time stamp recorded measuring information transmitting means, and the lapsed time information contained in the measuring information, or the measurement completion time is calculated by the server based on the time stamp recorded on the measuring information transmitted from the information terminal device, and the lapsed time information contained in the measuring information.

9. The data transmitter-receiver according to claim 8, wherein the predetermined information transmitted by said information transmitting means includes the time information of the data transmitter-receiver side synchronized by said data transmitter-receiver side synchronous means, when the data measuring instrument performs the synchronization with the time information, the time of the data measuring instrument is synchronized with the time information by the data measuring instrument.

10. The data transmitter-receiver according to claim 6, the time information is relative time on the basis of the predetermined time.

11. A measuring time management method using a server and an information terminal device connected to each other through a network, a data transmitter-receiver detachably connected with the information terminal device by a predetermined interface, and a data measuring instrument connected to the data transmitter-receiver by a predetermined wireless communication system, wherein the server includes a time information transmitting step for transmitting the time information of the server side to the information terminal device, the information terminal device includes an information terminal device side time information transmitting step for transmitting to the data transmitter-receiver the time information transmitted at said time information transmitting step, and the data transmitter-receiver includes a data transmitter-receiver side synchronous step for synchronizing the time of the data transmitter-receiver with the time information transmitted at said information terminal device side time information transmitting step and an information transmitting step for transmitting predetermined information to the data measuring instrument side, the data measuring instrument includes a measuring information transmitting step for transmitting the measuring information to the data transmitter-receiver, the data transmitter-receiver includes a time stamp record step for recording a time stamp on the measuring information transmitted at said measuring information transmitting step based on the time information of the data transmitter-receiver side synchronized at said data transmitter-receiver side synchronous step and a time stamp recorded measuring information transmitting step for transmitting to the information terminal device the measuring information on which the time stamp was recorded at said time stamp record step, and the information terminal device includes a measuring information forwarding step for forwarding to the server the measuring information transmitted at said time stamp recorded measuring information transmitting step.

12. The measuring time management method according to claim 11, wherein said measuring information transmitting step transmits to the data transmitter-receiver the measuring information performed predetermined operation to measured data based on the predetermined information transmitted at said information transmitting step.

13. The measuring time management method according to claim 11, wherein when the data measuring instrument transmits the measuring information after the lapse of predetermined time after measurement completion, the measuring information transmitted at said measuring information transmitting step contains lapsed time information showing lapsed time from the measurement completion to the transmission of the measuring information, the information terminal device includes a calculation step for calculating measurement completion time based on the time stamp recorded on the measuring information transmitted at said time stamp recorded measuring information transmitting step, and the lapsed time information contained in the measuring information, or the server includes the calculation step for calculating the measurement completion time based on the time stamp recorded on the measuring information forwarded at said measuring information forwarding step, and the lapsed time information contained in the measuring information.

14. The measuring time management method according to claim 13, wherein the predetermined information transmitted at said information transmitting step includes the time information of the data transmitter-receiver side synchronized at said data transmitter-receiver side synchronous step, and when the data measuring instrument performs the synchronization with the time information, the data measuring instrument further includes a data measuring instrument side synchronous step for synchronizing the time of the data measuring instrument with the time information prior to said measuring information transmitting step.

15. The measuring time management method according to claim 1, wherein the time information is relative time on the basis of the predetermined time.

* * * * *